US00PP33066P2

(12) United States Plant Patent
Mowrey et al.

(10) Patent No.: US PP33,066 P2
(45) Date of Patent: May 18, 2021

(54) BLUEBERRY PLANT NAMED 'DRISBLUETWENTYTWO'

(50) Latin Name: ***Vaccinium corymbosum* L.**
Varietal Denomination: DrisBlueTwentyTwo

(71) Applicant: Driscoll's, Inc., Watsonville, CA (US)

(72) Inventors: Bruce D. Mowrey, Watsonville, CA (US); Esther Kibbe, Watsonville, CA (US); Marta C. Baptista, Watsonville, CA (US); Raymond L. Jacobs, III, Watsonville, CA (US); Sarah Wool, Watsonville, CA (US); James Olmstead, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 2 days.

(21) Appl. No.: 16/873,056

(22) Filed: Jan. 23, 2020

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/08
See application file for complete search history.

(56) References Cited

U.S. PATENT DOCUMENTS

PP6,699 P 3/1989 Wood
PP11,807 P2 3/2001 Lyrene
PP12,783 P2 7/2002 Lyrene
PP15,146 P3 9/2004 Hancock
PP19,503 P3 * 11/2008 Lyrene ..... A01H 5/08 Plt./157
PP20,436 P2 10/2009 Caster et al.
PP20,449 P2 11/2009 Caster et al.
PP20,488 P2 11/2009 Caster et al.
PP24,407 P3 4/2014 Caster et al.
PP24,489 P3 5/2014 Caster et al.
PP24,568 P3 6/2014 Caster et al.
PP24,569 P3 6/2014 Caster et al.
PP24,605 P3 7/2014 Caster et al.
PP26,287 P3 1/2016 Caster et al.
PP26,451 P3 3/2016 Caster et al.
PP26,537 P3 3/2016 Caster et al.
PP26,643 P3 4/2016 Caster et al.
PP26,748 P3 5/2016 Caster et al.
PP27,622 P3 1/2017 Caster et al.
PP28,933 P2 2/2018 Caster et al.
PP31,698 P2 * 4/2020 Mowrey ..... A01H 5/08 Plt./157

OTHER PUBLICATIONS

Caster et al., Unpublished U.S. Appl. No. 16/602,840, filed Dec. 10, 2019, titled "Blueberry Plant Variety Named DrisBlueTwentyOne".
Caster et al., Unpublished U.S. Appl. No. 16/350,021, filed Sep. 13, 2018, titled "Blueberry Plant Variety Named'DrisBlueSeventeen'".
Caster et al. "Unpublished U.S. Appl. No. 16/501,199, filed Mar. 5, 2019, titled "Blueberry Plant Variety Named 'DrisBlueTwenty'"".
Mowrey et al., Unpublished U.S. Appl. No. 16/350,020, filed Sep. 13, 2018, titled "Blueberry Plant Variety Named 'DrisBlueSixteen'".
Mowrey et al., Unpublished U.S. Appl. No. 16/350,226, filed Oct. 16, 2018, titled "Blueberry Plant Variety Named 'DrisBlueNineteen'".

* cited by examiner

*Primary Examiner* — Kent L Bell
(74) *Attorney, Agent, or Firm* — Morrison & Foerster LLP

(57) ABSTRACT

A new and distinct variety of blueberry plant named 'DrisBlueTwentyTwo' is disclosed. 'DrisBlueTwentyTwo' was selected as a strong evergreen blueberry variety with early and high yield. Fruit of 'DrisBlueTwentyTwo' are large, with balanced sugars and acids, firm crisp texture, and good bloom. Plants of 'DrisBlueTwentyTwo' are precocious and fruit on both one-year-old and current season's shoots.

6 Drawing Sheets

Latin name:

Botanical classification: *Vaccinium corymbosum* L.

Varietal denomination: The varietal denomination of the claimed variety of blueberry plant is 'DrisBlueTwentyTwo'.

BACKGROUND OF THE INVENTION

Blueberry plants are perennial flowering plants with indigo-colored berries from the section Cyanococcus within the genus *Vaccinium*. Many commercially sold species with English common names, including blueberry, are currently classified in section Cyanococcus of the genus *Vaccinium* and come predominantly from North America. Many North American native species of blueberries are grown commercially in the Southern Hemisphere in Australia, New Zealand, and South American nations.

*Vaccinium corymbosum*, the northern highbush blueberry, is a North American species of blueberry which has become a food crop of significant economic importance. It is native to eastern Canada and the eastern and southern United States, from Ontario east to Nova Scotia and south as far as Florida and eastern Texas. It has been naturalized in Europe, Japan, New Zealand, and the Pacific Northwest of North America. Other common names include blue huckleberry, tall huckleberry, swamp huckleberry, high blueberry, and swamp blueberry.

Blueberries are usually erect, prostrate shrubs that can vary in size from approximately four inches to approximately 13 feet in height. In the commercial production of blueberries, the smaller species are known as "lowbush blueberries", while the larger species are known as "highbush blueberries".

Blueberry bushes typically bear fruit in the middle of the growing season. However, fruiting times can be affected by local conditions such as altitude and latitude. As such, peak crop can vary from May to August in the northern hemisphere, depending upon these conditions.

Blueberries are a popular fruit that is typically consumed as fresh fruit, individually quick frozen (IQF) fruit, or in prepared foods, such as purées, juices, jellies, jams, baked goods, snack foods, and cereals.

Blueberry is an important and valuable fruit crop. Accordingly, there is a need for new varieties of blueberry plant. In particular, there is a need for improved varieties of blueberry plant that are stable, high yielding, and agronomically sound.

SUMMARY OF THE INVENTION

In order to meet these needs, the present invention is directed to an improved variety of blueberry plant. In particular, the invention relates to a new and distinct variety of blueberry plant (*Vaccinium corymbosum* L.), which has been denominated as 'DrisBlueTwentyTwo'.

Blueberry plant variety 'DrisBlueTwentyTwo' was discovered in Hillsborough County, Fla. in April of 2013 and originated from a cross between the proprietary female parent blueberry plant '196H 3' (unpatented) and the proprietary male parent blueberry plant '7J301' (unpatented). The original seedling of the new variety was first asexually propagated via softwood cuttings in Santa Cruz County, Calif. in July of 2013.

'DrisBlueTwentyTwo' was subsequently asexually propagated via softwood cuttings and tissue culture and underwent further testing in Ventura County, Calif. for five years (2014 to 2019). The present blueberry variety has been found to be stable and reproduce true to type through successive asexual propagations via softwood cuttings and shoot tissue culture.

'DrisBlueTwentyTwo' exhibits the following distinguishing characteristics when grown under normal horticultural practices in Ventura County, Calif.:

1. Semi-upright plant growth habit;
2. Elliptic leaf shape; and
3. Entire leaf margin.

'DrisBlueTwentyTwo' was selected as a strong evergreen blueberry variety with early and high yield. Fruit of 'DrisBlueTwentyTwo' are large, with balanced sugars and acids, firm crisp texture, and good bloom. Plants of 'DrisBlueTwentyTwo' are precocious and fruit on both one-year-old and current season's shoots.

BRIEF DESCRIPTION OF THE DRAWINGS

This new blueberry plant variety is illustrated by the accompanying photographs. The colors shown are as true as can be reasonably obtained by conventional photographic procedures. The photographs are of plants that are four and a half years old, unless otherwise specified.

DETAILED BOTANICAL DESCRIPTION

Figure 1:
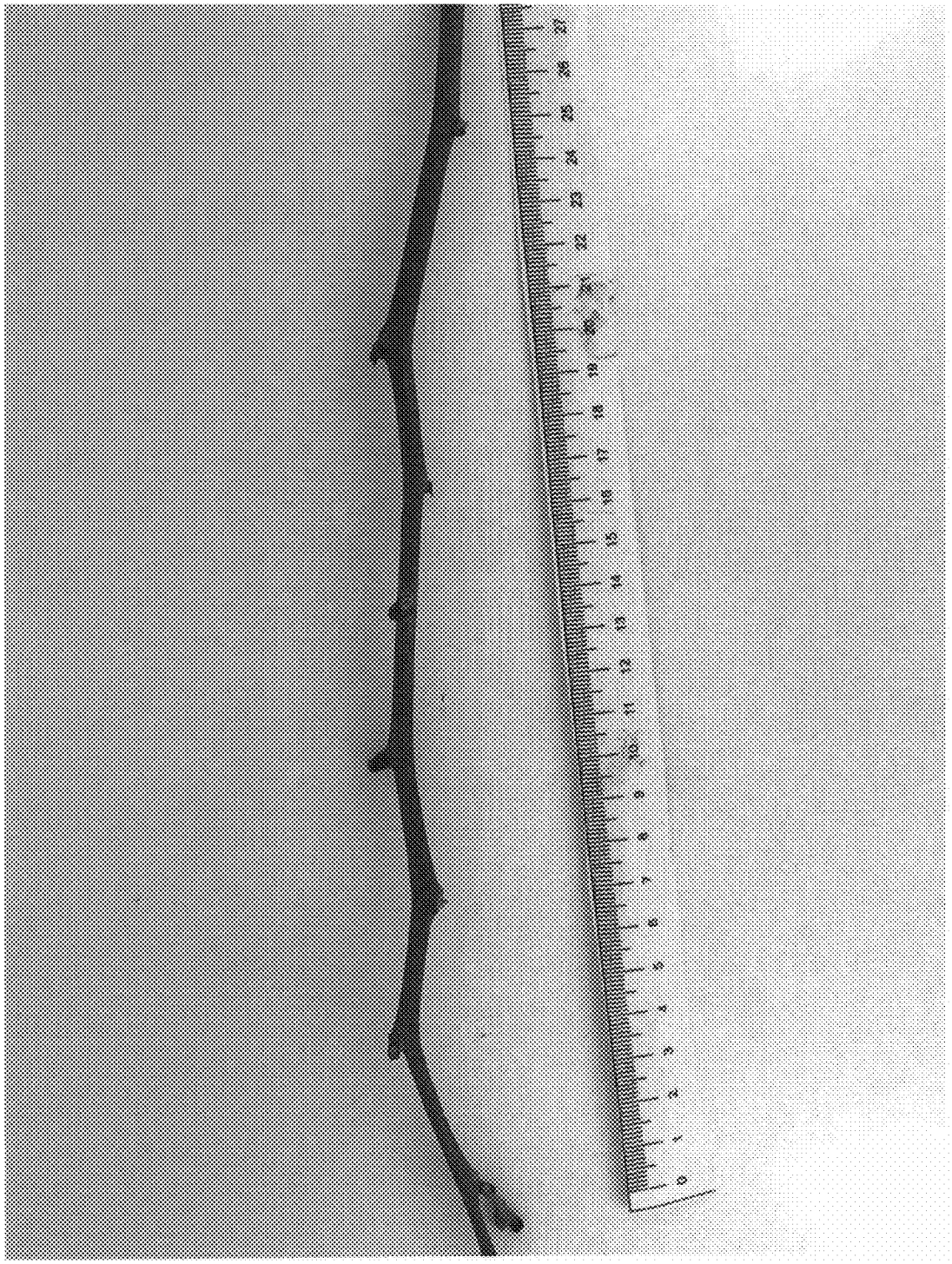
FIG. 1 illustrates a section of an immature cane of variety 'DrisBlueTwentyTwo'.
Figure 2:
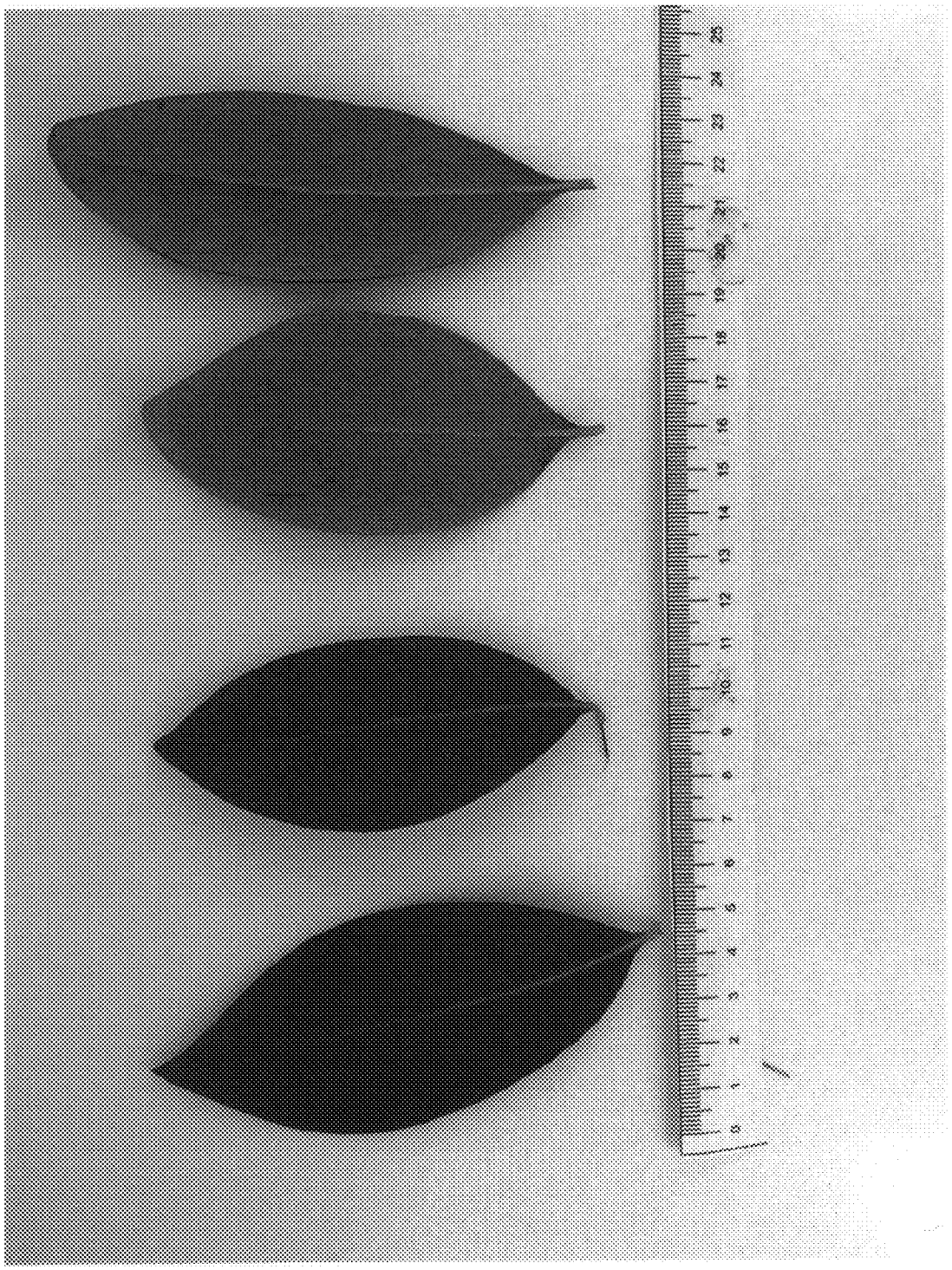
FIG. 2 illustrates leaves of variety 'DrisBlueTwentyTwo'. The two leaves on the left show the upper leaf surfaces and the two leaves on the right show the lower leaf surfaces.
Figure 3:
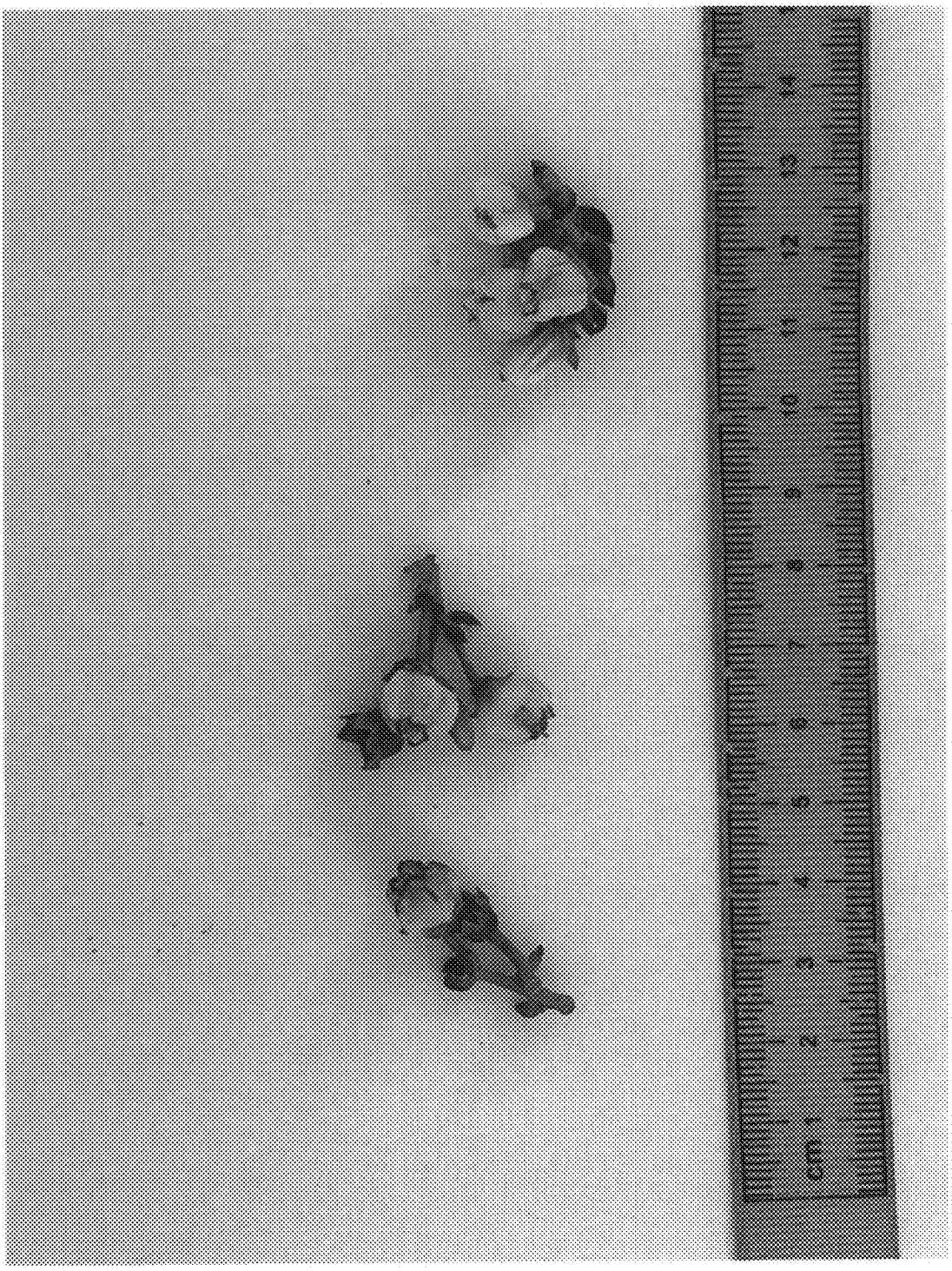
FIG. 3 illustrates clusters of flowers of variety 'DrisBlueTwentyTwo'.
Figure 4:
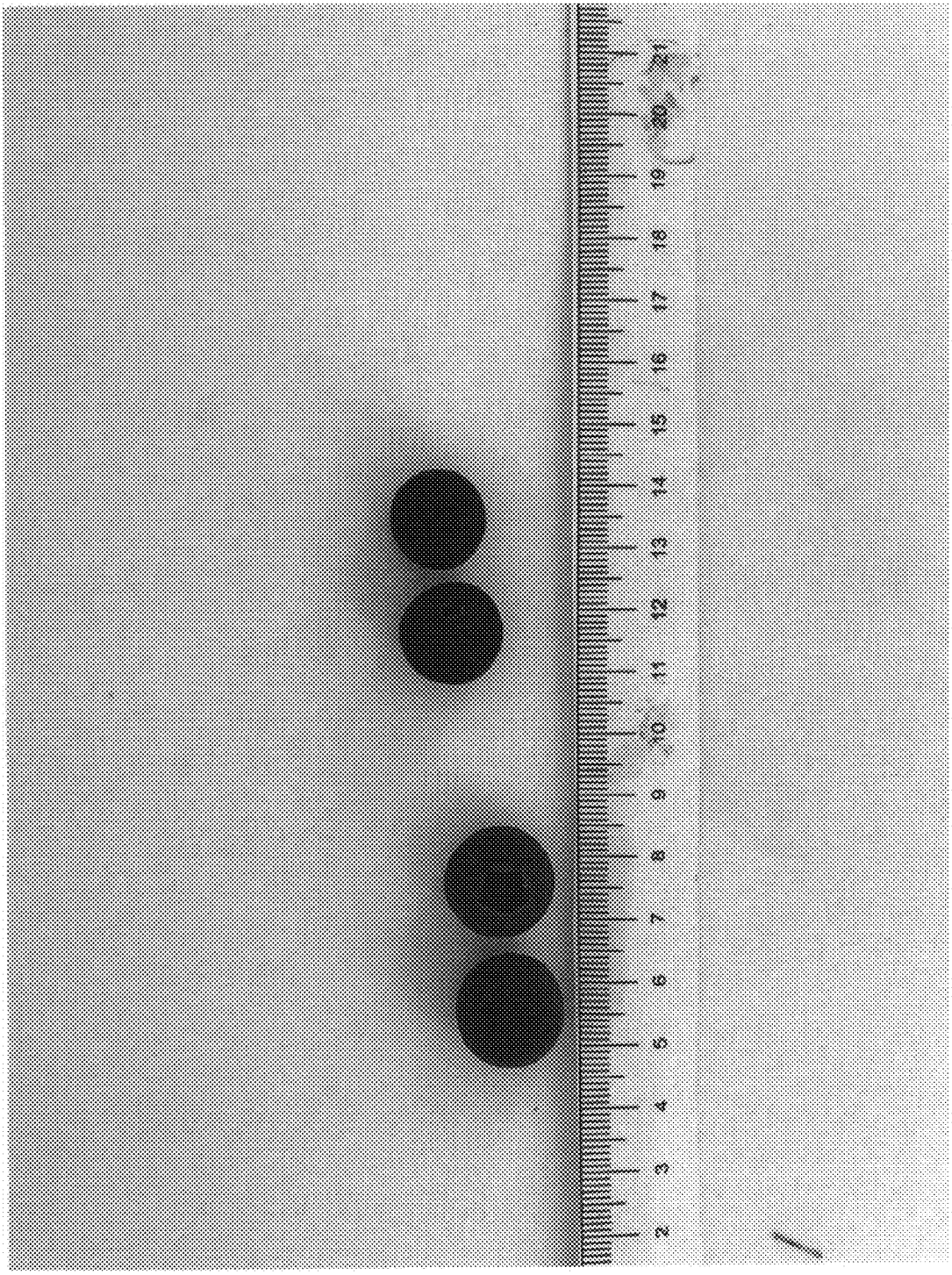
FIG. 4 illustrates whole fruit of variety 'DrisBlueTwentyTwo'. The two fruit on the left have bloom on them, and the two fruit on the right have bloom removed. Counting from left, the first and third fruit show the bottom view (fruit-pedicel junction) of the whole fruit, and the second and fourth fruit show the top view (calyx basin) of the whole fruit.
Figure 5:
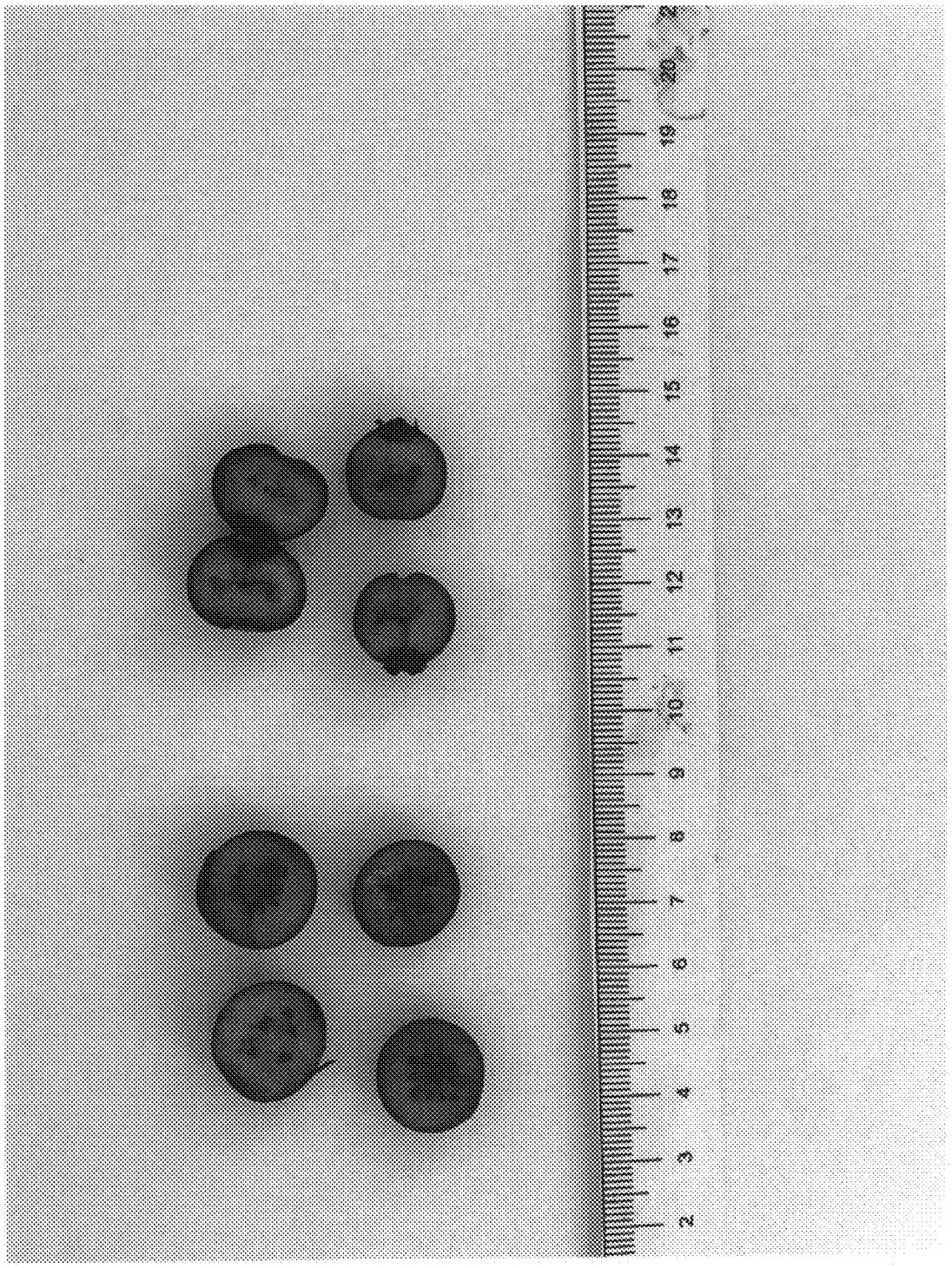
FIG. 5 illustrates the cross-sections (two columns of fruit on the left) and longitudinal sections (two columns of fruit on the right) of the fruit of variety 'DrisBlueTwentyTwo'.
Figure 6:
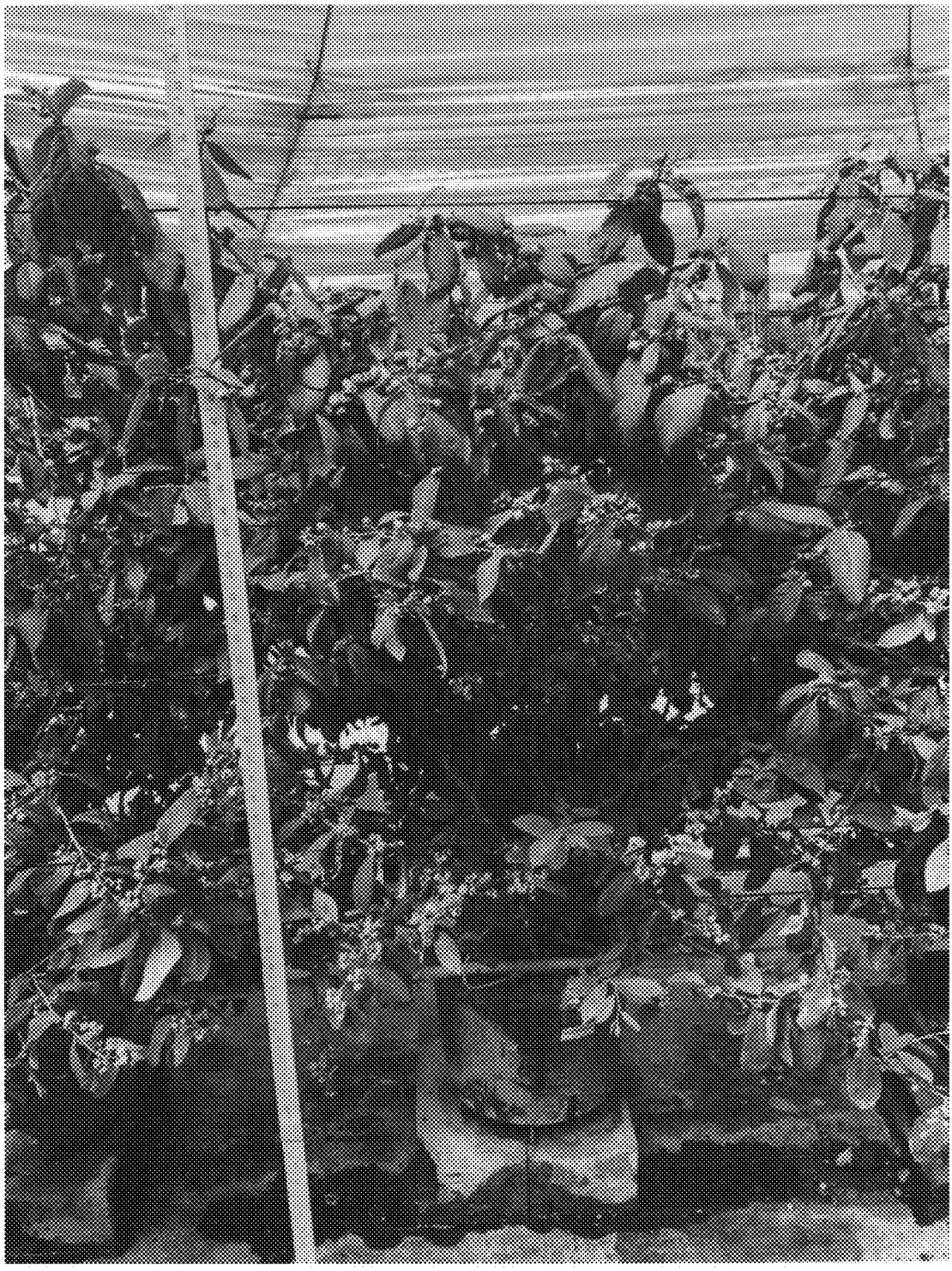
FIG. 6 illustrates plants of variety 'DrisBlueTwentyTwo'.

The following description sets forth the distinctive characteristics of 'DrisBlueTwentyTwo'. The data which define these characteristics is based on observations taken in Ventura County, Calif. from 2014 to 2019. This description is in accordance with UPOV terminology. Color designations, color descriptions, and other phenotypical descriptions may deviate from the stated values and descriptions depending upon variation in environmental, seasonal, climatic and cultural conditions. 'DrisBlueTwentyTwo' has not been observed under all possible environmental conditions. Unless noted otherwise, the botanical description of 'DrisBlueTwentyTwo' was taken from plants that were four and a half years old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* $2^{nd}$ edition by James G. Harris and Melinda Woolf Harris, unless where otherwise defined.

Classification:

*Family.*—Ericaceae.
*Botanical.*—*Vaccinium corymbosum* L.
*Common name.*—Blueberry.
*Variety name.*—'DrisBlueTwentyTwo'.

Parentage:

*Female parent.*—The proprietary blueberry plant '196H 3' (unpatented).
*Male parent.*—The proprietary blueberry plant '7J301' (unpatented).

Plant:

*Height.*—130.1 cm.
*Width.*—112.8 cm.
*Length/width ratio.*—1.2.
*Vigor.*—Strong.
*Growth habit.*—Semi-upright.
*Internode length.*—29.72 mm.
*One-year-old canes* (*young canes*).—Length: 68 cm. Diameter at the base: 9 mm. Diameter at the tip: 3 mm. Internode length on the upper half: 24.6 mm. Color: RHS 144A (Strong yellow-green). Texture: Smooth.
*Five-year-old canes* (*mature canes*).—Length: 83 cm. Diameter at the base: 26 mm. Diameter at the tip: 2 mm. Texture: Rough. Color: RHS 199D (Dark greyish yellow).

Leaves:

*Length.*—88.6 mm.
*Width.*—49.4 mm.

*Length/width ratio.*—1.8.
*Shape.*—Elliptic.
*Margin.*—Entire.
*Color on upper side.*—RHS 146A (Moderate olive green).
*Color of lower side.*—RHS 137C (Moderate yellow-green).
*Shape of the leaf apex.*—Acute.
*Shape of the leaf base.*—Cuneate.
*Texture of upper side.*—Smooth.
*Texture of lower side.*—Smooth.
*Petiole.*—Length: 6.5 mm. Diameter: 1.86 mm. Texture: Smooth. Color: RHS 145B (Light yellow-green).

Flowers:
*Inflorescence length (excluding peduncle).*—Short, 11.85 mm.
*Inflorescence width.*—7.21 mm.
*Flower length (excluding pedicel).*—9.58 mm.
*Flower diameter.*—8.25 mm.
*Flower length/width ratio.*—1.2.
*Flower bud.*—Length: 6 mm. Width: 4 mm. Number of flowers per bud: 6. Anthocyanin color: RHS 62A (Strong purplish pink).
*Flower pedicel.*—Length: 9.15 mm. Diameter: 1.84 mm. Texture: Smooth. Color: RHS 145A (Strong yellow-green).
*Corolla.*—Shape: Urceolate. Anthocyanin coloration of corolla tube: Absent or very weak. Anthocyanin color of corolla tube: RHS 158B (Pale yellow). Ridges on corolla tube: Absent. Petal width (ridge to ridge): 6.06 mm. Diameter of corolla aperture: 4.57 mm. Length of corolla tube: 8.81 mm. Corolla tube color: RHS 157D (Greenish white).
*Sepal.*—Number per flower: 7. Shape: Deltoid. Length: 6.85 mm. Width: 3.78 mm. Shape of apex: Acute. Margin: Entire. Texture of upper side: Smooth. Texture of lower side: Smooth. Color of upper side: RHS 138C (Moderate yellow-green). Color of lower side: RHS 138C (Moderate yellow-green).
*Reproductive organs.*—Style length (including stigma): 10.29 mm. Filament color: RHS 139D (Moderate yellow-green). Anther color: RHS N167B (Brownish orange). Style color: RHS 144A (Strong yellow-green). Ovary color: RHS 144A (Strong yellow-green). Pollen color: RHS 160C (Pale greenish yellow). Stamen length: 2.78 mm.
*Flowering interval on one-year-old shoot.*—November to May.
*Flowering interval on current season's shoot.*—November to May.

Fruit:
*Length.*—15.29 mm.
*Diameter.*—17.57 mm.
*Length/width ratio.*—0.9.
*Weight.*—2.7 grams.
*Shape in longitudinal section.*—Oblate.
*Attitude of sepals.*—Semi-erect.
*Type of sepals.*—Reflexed.
*Calyx basin.*—Diameter: 8.42 mm. Depth (including sepals): 2.18 mm. Diameter/depth ratio: 3.9.
*Number of berries per cluster.*—7.60.
*Fruit cluster peduncle length.*—11.38 mm.
*Fruit cluster peduncle diameter.*—1.29 mm.
*Fruit cluster peduncle texture.*—Smooth.
*Fruit cluster peduncle color.*—RHS 145A (Strong yellow-green).
*Diameter of fruit pedicel.*—1.90 mm.
*Length of fruit pedicel.*—6.89 mm.
*Texture of fruit pedicel.*—Smooth.
*Color of fruit pedicel.*—RHS 145A (Strong yellow-green).
*Color of unripe fruit.*—RHS 144C (Strong yellow-green).
*Color of fruit with bloom.*—RHS 98D (Light purplish blue).
*Color of fruit without bloom on mature fruit.*—RHS 202A (Dark greyish purple).
*Intensity of fruit bloom.*—Medium.
*Fruit flesh color.*—RHS 145C (Light yellow-green).
*Fruit firmness.*—Very firm.
*Fruit sweetness.*—Medium.
*Fruit acidity.*—Medium.
*Fruiting type.*—On one-year-old and current season's shoots.
*Ripening interval on one-year-old shoot.*—November to May.
*Ripening interval on current season's shoot.*—November to May.
*Fruit shipping quality and shelf life.*—Following harvest, fruit have been stored for 21 days when maintained under cooled temperatures (e.g. 4° C.) that are standard for blueberry storage.
*Market use.*—Fresh market use.
*Yield.*—25 tonnes to 40 tonnes of fruit per hectare per season from 24- to 36-month old plants when grown at Oxnard, Calif.

Resistance to abiotic stress, pests, and diseases:
*Drought.*—Moderately resistant.
*Heat.*—Moderately resistant.
*Cold.*—Plants have been grown in USDA Hardiness Zones 7-10.
*Blueberry bud mite (acalitus vaccinii).*—Moderately susceptible.
*Spotted-wing drosophila (drosophila suzukii).*—Moderately susceptible.
*Botrytis fruit rot (botrytis cinerea).*—Moderately susceptible.

COMPARISONS TO PARENTAL AND COMMERCIAL BLUEBERRY VARIETIES

'DrisBlueTwentyTwo' differs from the proprietary female parent '196H 3' (unpatented) in that fruit of 'DrisBlueTwentyTwo' have better firmness, picking scar, and shelf life than fruit of '196H 3'. Additionally, plants of 'DrisBlueTwentyTwo' mature earlier and are more productive than plants of '196H 3'.

'DrisBlueTwentyTwo' differs from the proprietary male parent '7J301' (unpatented) in that fruit of 'DrisBlueTwentyTwo' have better firmness than fruit of '7J301'. Additionally, plants of 'DrisBlueTwentyTwo' mature earlier and are more productive than plants of '7J301'.

'DrisBlueTwentyTwo' differs from commercial blueberry plant variety 'Snowchaser' (U.S. Plant Pat. No. 19,503) in that 'DrisBlueTwentyTwo' has a semi-upright plant growth habit, a green color of one-year-old shoot, an elliptic leaf shape, and an entire leaf margin, whereas 'Snowchaser' has an upright to spreading plant growth habit, a brown color of one-year-old shoot, an ovate leaf shape, and a serrate leaf margin.

'DrisBlueTwentyTwo' differs from the commercial blueberry plant variety 'DrisBlueNineteen' (U.S. Plant Pat. No. 31,698) in that 'DrisBlueTwentyTwo' has an elliptic leaf shape, ridges absent on corolla tube, an oblate fruit shape in longitudinal section, and reflexed fruit sepals, whereas 'DrisBlueNineteen' has an ovate leaf shape, ridges present on corolla tube, a round fruit shape in longitudinal section, and straight fruit sepals.

What is claimed is:

1. A new and distinct variety of blueberry plant designated 'DrisBlueTwentyTwo' as shown and described herein.

* * * * *